United States Patent
Karmaker et al.

(10) Patent No.: US 6,827,576 B2
(45) Date of Patent: *Dec. 7, 2004

(54) FIBER REINFORCED COMPOSITE POST

(75) Inventors: Ajit Karmaker, Wallingford, CT (US); Arun Prasad, Cheshire, CT (US)

(73) Assignee: Pentron Laboratory Technologies, LLC, Wallingford, CT (US)

( * ) Notice: Subject to any disclaimer, the term of this patent is extended or adjusted under 35 U.S.C. 154(b) by 60 days.

This patent is subject to a terminal disclaimer.

(21) Appl. No.: 10/184,353

(22) Filed: Jun. 26, 2002

(65) Prior Publication Data

US 2003/0027102 A1 Feb. 6, 2003

Related U.S. Application Data

(63) Continuation of application No. 09/718,617, filed on Nov. 22, 2000, now Pat. No. 6,439,890, which is a continuation of application No. 09/280,760, filed on Mar. 29, 1999, now Pat. No. 6,186,791, which is a continuation-in-part of application No. 09/249,864, filed on Feb. 16, 1999, now abandoned.

(60) Provisional application No. 60/096,587, filed on Aug. 14, 1998, and provisional application No. 60/096,020, filed on Aug. 11, 1998.

(51) Int. Cl.$^7$ .................................................. A61C 5/08
(52) U.S. Cl. ...................................................... 433/220
(58) Field of Search ............................... 433/220, 221, 433/224, 225, 211

(56) References Cited

U.S. PATENT DOCUMENTS 5,797,748 A * 8/1998 Reynaud et al. ............. 433/224
5,964,592 A * 10/1999 Hites et al. .................. 433/221

* cited by examiner

Primary Examiner—Kevin Shaver
Assistant Examiner—Melba Bumgarner
(74) Attorney, Agent, or Firm—Ann M. Knab

(57) ABSTRACT

A dental post comprising a rod fabricated of fiber-reinforced composite material. The rod comprises a plurality of frustoconical sections arranged coaxially along the longitudinal axis of the rod. Preferably the rod has consistent width along the longitudinal axis wherein the frustoconical sections each have the same tapered width and same length. The number of frustoconical units per rod can vary. The frustoconical sections may vary in shape. Moreover, the rod may include a channel therein extending along the longitudinal axis thereof. The rod may also include one or more grooves extending along the surface thereof.

7 Claims, 1 Drawing Sheet ns and claims priority to Provisional Application Ser. No. 60/096,020 filed Aug. 11, 1998 and Provisional Application Ser. No. 60/096,587 filed Aug. 14, 1998, all which are hereby incorporated by reference.

FIELD OF THE INVENTION

The present invention relates generally to endodontic posts and pins and more specifically to endodontic posts and pins fabricated of fiber reinforced composite material.

BACKGROUND OF THE INVENTION

Conventional endodontic posts are typically fabricated of metals or metal alloys. The metallic posts fabricated of less noble alloys can cause electro-chemical corrosion and weaken the restoration. In the natural tooth, the elastic modulus of dentin in the crown portion is about 20 GPa, and at root portion is about 9 to 10 GPa. The mismatch of the elastic moduli of metallic post and dentin very often initiates dentine fracture, especially at the apex of the root. Additionally, many conventional dowel pins are threaded and must be screwed into dentin. This can also increase the potential for weakening and eventual fracture of the tooth.

There is a need to provide aesthetically pleasing posts and pins. It is desirable that the posts and pins are rigid and strong to support the stresses occurring in the mouth. It is important that the posts and pins are compatible with the properties of the endodontic materials in the mouth.

SUMMARY OF THE INVENTION

These and other objects and advantages are accomplished by the post and pins of the present invention comprising a rod fabricated of fiber-reinforced composite material. The rod comprises a plurality of frustoconical sections arranged coaxially along the longitudinal axis of the rod. Preferably the rod has consistent width along the longititudinal axis wherein the frustoconical sections each have the same tapered width and same length. The number of frustoconical units per rod can vary. The frustoconical sections may vary in shape. Moreover, the rod may include a channel therein extending along the longitudinal axis thereof. The rod may also include one or more grooves or flat surfaces extending along the surface thereof. In another embodiment, the post may include a portion of fibers or alternatively, all of the fibers, that are either pigmented or inherently colored to enable identification of the post inside the mouth.

The material formulation and surface design of the post of the invention are beneficial because the matrix resin of the post, filling material between the post and the root canal, and the core material disposed on top of the post, all contain the same or very similar chemical components. This enables better chemical bonding of the system. Furthermore, the rough surface structures of the post promote chemical bonding as well as mechanical anchors, resulting in a better retention of the post.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
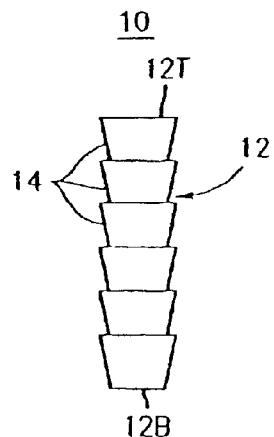
FIG. 1 is an elevational view of a post in accordance with the invention.

FIG. 1 shows a post 10 which includes a rod 12. Rod 12 comprises a plurality of frustoconical sections 14 arranged coaxially along the longitudinal axis of rod 12. Preferably rod 12 has consistent width along the longitudinal axis wherein frustoconical sections 14 each have the same tapered width and same length. It is possible to vary the width and/or length of rod 12 wherein the tapered width and/or length of frustoconical sections 14 vary along the longitudinal axis of rod 12. The ratio of the maximum diameter (top side) to the minimum diameter (bottom side) of the frustoconical sections is between about 1.0 and about 2.0 and is preferably between about 1.0 and about 1.5. The number of frustoconical units 14 per rod can vary. Preferably, an 18 mm post comprises between about 9 to about 10 units providing a pitch of about 2 mm.

Figure 2:
FIG. 2 is an elevational view of one embodiment of the frustoconical sections of the post of the present invention.
Figure 3:
FIG. 3 is an elevational view of another embodiment of the frustoconical sections of the post of the present invention.
Figure 4:
FIG. 4 is an elevational view of a third embodiment of the frustoconical sections of the post of the present invention.

FIGS. 2, 3 and 4 show variations 14A, 14B and 14C of frustoconical sections 14. In FIG. 2, the walls of section 14A taper outwardly from the bottom to the top side. In FIG. 3, the walls of section 14B taper outwardly from the bottom to a point proximate the top side and continue in a constant width to the top side to provide a more truncated version of frustoconical sections 14. In FIG. 4, the walls of section 14C taper outwardly from the bottom to a point proximate the top side and curve inwardly therefrom to the top side to provide a more rounded version of frustoconical sections 14.

Figure 5:
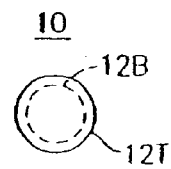
FIG. 5 is a top plan view of the post of FIG. 1.

FIG. 5 is a top plan view of post 10 wherein the inner dotted line 12B represents the diameter of the bottom side of rod 12 and outer edge 12T represents the top side of rod 12.

Figures 6, 7:
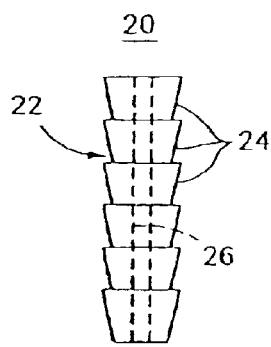
FIG. 6 is an elevational view of a second embodiment of a post in accordance with the invention.
FIG. 7 is a top plan view of the post of FIG. 6.

FIG. 6 is directed to a second embodiment of the post of the invention wherein post 20 includes a rod 22. Rod 22 comprises a plurality of frustoconical sections 24 arranged coaxially along the longitudinal axis of rod 22. Preferably, rod 22 has consistent width along the longitudinal axis thereof wherein frustoconical sections 24 each have the same tapered width and same length. It is possible to vary the width and/or length of rod 22 wherein the tapered width and/or length of frustoconical sections 24 vary along the longitudinal axis of rod 22. Rod 22 includes a channel 26 extending along the longitudinal axis thereof. FIG. 7 is a top plan view of post 20 wherein the inner dotted line 22B represents the diameter of the bottom side of rod 22 and outer edge 22T represents the top side of rod 22.

Figures 8, 9:
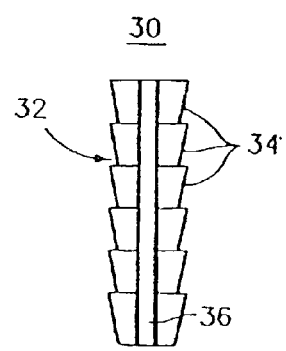
FIG. 8 is an elevational view of a third embodiment of a post in accordance with the invention.
FIG. 9 is a top plan view of the post of FIG. 8.
Figure 10:
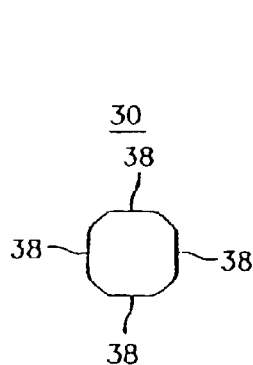
FIG. 10 is a top plan view of an alternative embodiment of the post of FIG. 9.

FIG. 8 is directed to a third embodiment of the post of the invention wherein post 30 includes a rod 32. Rod 32 comprises a plurality of frustoconical sections 34 arranged coaxially along the longitudinal axis of rod 32. Preferably, rod 32 has consistent width along the longitudinal axis thereof whereas frustoconical sections 34 each have the same tapered width and same length. It is possible to vary the width and/or length of rod 32 wherein the tapered width and/or length of frustoconical sections 34 vary along the longitudinal axis of rod 32. Rod 32 further includes a series of grooves 36 extending along the length of rod 32 and positioned approximately ninety degrees apart. It is possible that more or fewer grooves 36 be disposed on rod 32 and the spacing thereof may vary. Alternatively, in place of the grooves, 36 the rod may include one or more flat surfaces along the length thereof. FIG. 9 is a top plan view of post 30 wherein the inner dotted line 32B represents the diameter of the bottom side of rod 32 and outer edge 32T represents the top side of rod 32 and grooves 36 are spaced at ninety degree intervals. FIG. 10 shows a top plan view of post 30 with flat surfaces 38 along the length thereof.

In accordance with another embodiment of the invention, the post may be of a solid rod of circular or other suitable cross-section, without any grooves or steps on the outer surface. Moreover, the post may include a larger head of any shape with or without a retentive design to provide support for a core thereon.

Figure 11:
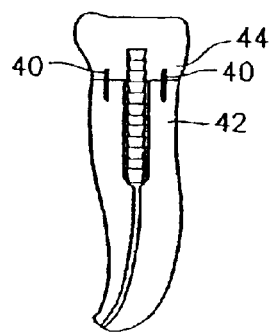
FIG. 11 is an elevational view of a tooth having a post and pins therein.

In accordance with yet another embodiment of the invention, fiber-reinforced composite rods of about 0.5 to about 0.6 mm in diameter are used as dowel pins to improve the retention against rotational movement. The pins are preferably solid and have a circular cross-section although other suitable cross-sectional configurations may be utilized. Reference is made to FIG. 11 showing pins 40 positioned in dentin 42 and core material 44. Pins 40 can be placed vertically or at any angle to connect the core and the remaining dental structure. Pins 40 are rod-shaped units which may include threading thereon to aid the retention of the restoration to the tooth. They differ from posts in that they are much smaller and are placed in solid dentin, not the root canal. Pins 40 are preferably bonded in place so the tooth is not further compromised due to screwing or like placement of the pins into the dentin.

Figure 12:
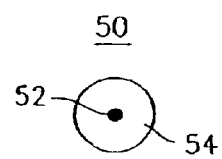
FIG. 12 is a top plan view of the post having a portion of the fibers pigmented.

In accordance with another embodiment herein, the post may include a one or more of the impregnated fibers having a color distinct from the remainder of the fibers forming the post to assist in the identification of the post in the mouth. FIG. 12 shows a post 50 having a section of the fibers 52 centrally located of a different or darker color than the remainder of the fibers 54. The fibers 54 may be any transparent, translucent, or opaque color such as a white color and the colored section 52 of the fibers may be of any transparent, translucent or opaque color which is distinguishable from the white or like color of fibers 54. The fibers may be colored during or after manufacture of the post or the fibers may be inherently of a color such as carbon fibers which exhibit a dark color, typically a black or brown color. In accordance with a method of making the colored posts herein, the fibers to be colored may be colored simultaneously during the manufacture of the post or after the post has been manufactured. Preferably, the coloring is performed during manufacture of the post. If the pultrusion method is used, pigments may be added to resin material. A section of fibers which form the post are then impregnated with the pigment containing resin material. The remaining fibers are impregnated with pigment-free resin material. The post is then molded from the pigmented (or inherently colored) and non-pigmented fibers and cured. Alternatively, all of the fibers are impregnated with resin material and thereafter a portion of fibers are coated with a pigment and the post is then molded from the pigmented and non-pigmented fibers and cured. The colored fiber bundle may be concentrically or non-concentrically located.

This technique may also be used for any composite resin post design and is not limited to the design described herein. The composite resin may include any of the materials mentioned herein. Additionally, this technique may be used in the manufacture of ceramic posts. The ceramic post may include any ceramic materials including but not limited to alumina, zirconia, mullite, silica, leucite and carbides and may be fabricated by using any forming and sintering techniques. The differently colored section provides easy detection of the post in the mouth.

The post and pins, in accordance with the present invention, are preferably fabricated of fiber-reinforced composite material comprising a polymeric matrix and reinforcing fibers within the matrix. The fibers are embedded in the matrix manually or mechanically by a variety of techniques including, but not limited to matched die processes, autoclave molding, resin injection molding (RIM), sheet, dough and bulk molding, press molding, injection molding, reaction injection molding, resin transfer molding (RTM), compression molding, open molding, extrusion, pultrusion and filament winding. U.S. Pat. Nos. 4,717,341 and 4,894,012 to Goldberg et al. show methods of impregnation and are hereby incorporated by reference. In acccordance with one embodiment of the invention, the fiber-reinforced polymeric matrix is formed using the pultrusion or filament winding technique whereby the fibers are pre-impregnated with particulate filled resin and passed or pressed through a combination of dies or molds to shape the fiber-reinforced polymeric matrix material into a rod. The rods are preferably straight and are of circular cross-section although the cross-section may be of any shape suitable for use as a post to fit within the root canal (or the pins to fit within the dentin). As the rod-shaped fiber-reinforced polymeric matrix material exits the last die, it is cured by conventional means, preferably by visible light. The prepared rods may be further light and heat cured to ensure the maximum cross-linking of monomers. Alternatively, the rods may be cured inside the die by light and/or heat. Thereafter, the rod-shaped material may be further shaped by known means such as for example by machining, cutting, carving or grinding. Preferably, the rod-shaped material is surface-modified by a screw machine, centerless grinding machine or like means to provide the frustoconical sections thereon. The rod-shaped material may be cut into smaller ready-to-use units at any time in the fabrication process, preferably before or after the surface-modifying step. The post created may further be coated with a filled or unfilled resin and/or grafted with a coupling agent.

The polymeric matrix element of the composite is selected from those known in the art of dental materials, including but not being limited to polyamides, polyesters, polyolefins, polyimides, polyacrylates, polyurethanes, vinyl esters or epoxy-based materials. Other polymeric matrices include styrenes, stryrene acrylonitriles, ABS polymers, polysulfones, polyacetals, polycarbonates, polyphenylene sulfides, and the like.

Preferred polymeric materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") are also commonly-used principal polymers suitable for use in the present invention.

The polymeric matrix typically includes polymerization initiators, polymerization accelerators, ultraviolet light absorbers, anti-oxidants, and other additives well known in the art. The polymeric matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred polymeric matrix is a curable matrix, wherein light cure effects partial cure of the matrix, and final curing is by heat under controlled atmosphere. Radiopaque agents may be included in the matrix. Preferably, barium sulfate is present in an amount of about 5 to about 20% by weight with particle sizes ranging from about 0.1 to about 2 microns.

The polymeric matrix may further comprise at least one filler known in the art and used in dental restorative materials, the amount of such filler being determined by the specific use of the fiber-reinforced composite. Generally, the filler is added in an amount of up to about seventy percent by weight of the composite and preferably in an amount of up to about thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, barium sulfate, barium molybdate, barium methacrylate, barium ytrrium alkoxy ($Ba_2Y(OR)_x$), strontium silicate, barium borosilicate, strontium borosilicate, borosilicate, lithium silicate, amorphous silica, ammoniated or deammoniated calcium phosphate and alumina, zirconia, tin oxide, tantalum oxide, niobium oxide, and titania. Particularly suitable fillers for dental filling-type materials prepared in accordance with this invention are those having a particle size ranging from about 0.1–5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and No. 4,547,531 to Waknine, the pertinent portions of which are incorporated herein by reference.

Suitable organic filler materials are known in the art, including for example the poly(methacrylate) fillers described in U.S. Pat. No. 3,715,331 to Molnar. A mixture of organic and inorganic filler materials may also be used.

The reinforcing fiber element of the composite preferably comprises glass, carbon, graphite, polyaramid, or other fibers known in the art, such as polyesters, polyamides, and other natural and synthetic materials compatible with the polymeric matrix. Some of the aforementioned fibrous materials and filler materials are disclosed in commonly assigned copending U.S. patent application Ser. Nos. 08/907,177, now abandoned, 09/059,492, now abandoned, No. 60/055,590, now U.S. Pat. No. 6,039,569, Ser. No. 08/951,414, now U.S. Pat. No. 6,013,694 and U.S. Pat. Nos. 4,717,341 and 4,894,012 all which are incorporated herein by reference. The fibers may further be treated, for example, chemically or mechanically etched, silanized, or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, NY.

The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension. The fibrous element may optionally take the form of a fabric. Fabric may be of the woven or non-woven type and is preferably preimpregnated with a polymeric material as set forth above. Examples of suitable woven fabric materials include but are not limited to those known in the art such as E glass and S glass fabrics and reinforcement fabrics sold by NFGS Inc. of New Hampshire under the style numbers 6522 and 7581. One preferred non-woven fabric material is available under the name Glass Tissue (20103A) from Technical Fibre Products Ltd. of Slate Hill, N.Y. The fibrous component may be present in the fiber reinforced composite material in the range from about 20% to about 85% of the composite, and more preferably between about 30% to about 65% by weight.

The post may be fabricated to be anisotropic or isotropic with respect to its properties. This is accomplished by various combinations of materials to achieve the desired properties. The flexural modulus of the post of the invention is between about 10 and about 30 GPa, depending on the mode of applied load (tensile or bending) and preferably between about 10 and about 20 GPa. The post has a low elastic modulus to minimize the mismatch between the post and the root. The bond strength of the post is between about 15 and about 40 MPa and preferably about 20 MPa. The flexural strength is between about 800 and about 1000 MPa and preferably about 850 MPa. The material formulation and surface design of the post of the invention are beneficial because the matrix resin of the post, filling material between the post and the root canal, and the core material disposed on top of the post, all contain the same or very similar chemical components. This enables better chemical bonding of the system. Furthermore, the rough surface structures of the post promote chemical bonding as well as mechanical anchors, resulting in a better retention of the post. The following Example illustrates the properties of the post of the invention.

EXAMPLE

Bond strength and flexural properties were measured on a post having a diameter of about 1.41 mm with a support length of 12 mm. Three-point bend testing was used to calculate flexural strength and flexural modulus on ten posts. The average flexural strength was about 960 MPa with a standard deviation of 90 and the average flexural modulus was about 13.5 GPa with a standard deviation of 1.1. Bond strength was measured between the post and a cementing material on five posts which were air-abraded prior to testing. Thereafter, testing was conducted on posts with (1) no subsequent treatment; (2) silane treatment; and (3) application of bonding agent (Bond-1® available from Jeneric/Pentron Inc., Wallingford, Conn.). The average bond strength for the untreated posts was about 23.2 MPa with a standard deviation of 8.1. The average bond strength of the silane-treated posts was about 28.0 MPa with a standard deviation of 8.8 and the average bond strength of the posts with a bonding agent thereon was about 26.5 MPa having a standard deviation of 6.8.

The posts of the present invention can be used to prepare customized posts in a variety of ways. The post or rod may be further machined, ground, or cut to form a post having a pin section and head portion. A core is then built on top of the head portion of the post with a dental resin material. The dental resin material is typically a composite material comprising fillers bound together by a polymeric matrix. Examples of polymeric materials are disclosed in U.S. Pat. Nos. 3,066,112, 3,179,623 and 3,194,784 to Bowen; U.S. Pat. Nos. 3,751,399 and 3,926,906 to Lee et al; and commonly assigned U.S. Pat. No. 5,276,068 to Waknine, all of which are incorporated by reference herein. Suitable fillers include those being covalently bonded to the polymeric matrix such as those disclosed in commonly assigned U.S. Pat. Nos. 4,547,531 and 4,544,359 to Waknine, both incorporated by reference herein. A preferred dental resin material is Sculpture® composite material, sold by Jeneric/Pentron, Inc., Wallingford, Conn., which may be cured with light, heat or the combination. The post and core are then bonded to the tooth canal preferably with a polymerizable adhesive and cement.

As will be appreciated, the present invention provides fiber-reinforced posts and pins useful in the fabrication of dental restorations. The posts include frustoconical sections which aid in the retention of the post in the canal. Pins are also provided to aid in the retention of the dental restoration to the dentin surrounding the root canal. Kits may also be provided with posts and pins of varying lengths and diameters offering many options to the technician and practitioner.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental post comprising:
   a longitudinally extending rod;
   wherein the rod is fabricated of fiber-reinforced composite material comprising a plurality of fibers impregnated with a polymeric matrix;
   wherein the plurality of fibers that are impregnated with a polymeric matrix are aligned along the longitudinal dimension of the rod;
   wherein the plurality of fibers that are aligned along the longitudinal dimension of the rod comprise one or more fibers of a color different than the color of a remainder of the plurality of fibers that are aligned along the longitudinal dimension in the fiber-reinforced composite material; and
   wherein the one or more fibers of the different color are centrally located with respect to the remainder of the fibers in the fiber-reinforced composite material.

2. The dental post of claim 1 wherein the plurality of fibers comprise transparent, translucent, or opaque fibers, or a mixture thereof.

3. The dental post of claim 2 wherein the plurality of fibers comprise white fibers.

4. The dental post of claim 1 wherein the one or more fibers of the different color comprise transparent, translucent, or opaque fibers, or a mixture thereof.

5. The dental post of claim 4 wherein the one or more fibers of the different color comprise white fibers.

6. A dental post comprising:
   a longitudinally extending rod;
   wherein the rod is fabricated of a material consisting essentially of ceramic material;
   wherein a section of the rod is of a color different than a color of a reminder of the rod; and
   wherein the section of the rod that is a different color is centrally located with respect to the remainder of the rod.

7. The dental post of claim 6 wherein the ceramic material comprises alumina, zirconia, mullite, silica, leucite, silicon carbide or a mixture thereof.

* * * * *